United States Patent
Lotz et al.

(10) Patent No.: US 8,309,159 B2
(45) Date of Patent: Nov. 13, 2012

(54) PROCESS FOR OBTAINING LEGUME PROTEIN FRACTIONS OF MODERATE MOLECULAR WEIGHT, LEGUME PROTEIN FRACTIONS AND USE THEREOF

(75) Inventors: Martin Lotz, Emlichheim (DE); Gerold Eggengoor, Wilsum (DE)

(73) Assignee: Emsland-Staerke GmbH, Emlichheim (DE)

( * ) Notice: Subject to any disclaimer, the term of this patent is extended or adjusted under 35 U.S.C. 154(b) by 458 days.

(21) Appl. No.: 12/447,341

(22) PCT Filed: Sep. 24, 2007

(86) PCT No.: PCT/DE2007/001724
§ 371 (c)(1),
(2), (4) Date: Apr. 27, 2009

(87) PCT Pub. No.: WO2008/049385
PCT Pub. Date: May 2, 2008

(65) Prior Publication Data
US 2010/0063254 A1  Mar. 11, 2010

(30) Foreign Application Priority Data
Oct. 26, 2006  (DE) .......................... 10 2006 050 619

(51) Int. Cl.
*A23J 1/00* (2006.01)
*C07K 14/00* (2006.01)
(52) U.S. Cl. ........................................... 426/656; 514/2
(58) Field of Classification Search .................... None
See application file for complete search history.

(56) References Cited

U.S. PATENT DOCUMENTS

| | | | |
|---|---|---|---|
| 4,066,633 A | | 1/1978 | Gastineau et al. |
| 4,766,204 A | | 8/1988 | Nickel |
| 5,034,227 A | | 7/1991 | Nickel |
| 5,597,607 A | * | 1/1997 | Samoto et al. ................ 426/656 |
| 7,186,807 B2 | | 3/2007 | Salome et al. |
| 2008/0226810 A1 | * | 9/2008 | Passe et al. ................... 426/656 |
| 2008/0226811 A1 | | 9/2008 | Boursier et al. |

FOREIGN PATENT DOCUMENTS

| DE | 100 24 838 A1 | 11/2001 |
|---|---|---|
| WO | 83/03952 A1 | 11/1983 |
| WO | 2007/017571 A1 | 2/2007 |

OTHER PUBLICATIONS

International Search Report for International Application No. PCT/DE2007/001724.
Francesca E. O'Kane et al., Characterization of PEA Vinclin. 1. Denoting Convicilin as the α-Subunit of the Pisum Vicilin Family, Journal of Argricultural and Food Chemistra, vol. 52, No. 10, 2004, pp. 3141-3148.
Pratap Chakraborty et al.,Ultracentrifugation of Salt-Soluble Proteins in Ten Legume Species, Journal of the Science of Food Chemistra, vol. 30, No. 8, 1979, pp. 766-771.
English Translation of the International Preliminary Report on Patentability and Written Opinion of the International Searching Authority for International Application No. PCT/DE2007/001724.
A.K. Sumner et al., Production and Evaulluation of PEA Protein Isolate; Journal of Food Science, vol. 46, 1981, pp. 364-366 and 372.

* cited by examiner

*Primary Examiner* — Anand Desai
(74) *Attorney, Agent, or Firm* — Roberts Mlotkowski Safran & Cole, P.C.; David S. Safran

(57) ABSTRACT

A process for producing coagulated leguminous protein fractions of MW>14, comprising: initial charging of fruit juice; coagulation of the leguminous protein; removal of a leguminous protein fraction whose majority has an MW of from >14 kD to approx. 600 kD; optionally, washing the coagulated leguminous protein fraction thus obtained; and optionally, drying the leguminous protein fraction, and to the use of the leguminous protein fraction as a food, food additive, medicament additive, animal feed, in cosmetics, as industrial protein, and/or as an adhesive.

7 Claims, No Drawings

PROCESS FOR OBTAINING LEGUME PROTEIN FRACTIONS OF MODERATE MOLECULAR WEIGHT, LEGUME PROTEIN FRACTIONS AND USE THEREOF

BACKGROUND OF THE INVENTION

1. Field of Invention

The invention relates to a method of obtaining coagulated legume fruit protein fractions having a molecular weight of greater than 14, to coagulated legume fruit protein fractions with a molecular weight greater than 14 and less than or equal to 600, and to the use thereof. Thus, the invention relates to obtaining plant proteins, the plant proteins themselves as well as the use of these proteins.

2. Description of Related Art

Proteins are vital chemical compounds for the entire living world, mostly with biochemical functions as enzymes, but also as storage substance (storage proteins), so to say as resource reservoir for vitally important processes, primarily for growth and/or reproduction processes. Proteins are characterized by their molecular size, their composition as well as their secondary and tertiary structure. We talk of proteins if the chemical structure consists exclusively of amino acids and the chain length amounts to approximately 30 or more amino acids. Shorter chains are usually called peptides. However, there is actually no exact definition of this classification. It is rather arbitrary and only useful for some individual situations. Proteins are generated by mono-cellular creatures, e.g., bacteria and yeasts, plants but also by animals. They are indispensable to human and animal nutrition as well as health. Besides their chemical, nutritive and biochemical characteristics, proteins possess also so-called functional characteristics. Features like their water absorption capability, digestibility, water solubility, the creation and stabilization of foam as well as their emulsifying capabilities are characterized by the tertiary and secondary structure and make them applicable for technical applications. Thus, proteins are used in many technical fields, for instance as glue, emulsifying and thickening agents. If exposed to heat or acids or alkali their tertiary structure is severely and often irreversibly damaged. The secondary structure is destroyed by proteolysis occurring due to enzymes or highly alkaline or acid mediums. Thus, it is very important to maintain the proteins' functional characteristics during their isolation.

SUMMARY OF THE INVENTION

State of the technology is to isolate both animal and plant proteins. They are already used in manifold application fields, e.g., as in food (tofu), animal feed, in pharmacy and technical applications (protein glue or similar). The protein's significance to nutrition, food technology, e.g., as foaming agent, emulsifying agent, structure enhancing and/or texturing agent (e.g., gelatin for gummy bears and glaze), animal feed, cosmetics and medical products is unique and cannot be substituted by any other substance class. The easiest way to obtain such functional proteins which posses good water solubility and emulsifying capabilities is to use those obtainable from milk or eggs (no heavy changes in pH value, no high temperatures).

It is a problem that especially animal proteins often trigger allergic reactions.

Cow milk proteins which are used quite frequently are feared by many consumers suffering from lactose intolerance or who are allergic to cow milk proteins. Additionally, animal proteins have the disadvantage carrying possible diseases (such as BSE, HIV or avian flu) or that they could be pathogen. Another disadvantage of animal proteins is that, due to ethical reasons, they are often not accepted by many population groups. For instance, skin creams which are based on collagen are proscribed in Asian and Muslim cultures for exactly these grounds. However, even in our cultures, they cause various allergies. Furthermore, animal proteins are normally more expensive than plant proteins because plant proteins are by far more sustainable than animal proteins—plant proteins are cheaper to produce and are ideal for vegetarian or any other diets such as purine-reduced diets or nutrition. Thus, it makes sense to examine plant proteins in more detail.

Plant proteins, in particular legume proteins, such as pea proteins and field bean proteins, avoid many of the above mentioned disadvantages of animal proteins. Many of them are hardly or not allergenic, i.e., they are not registered in the allergen list of the EU, are accepted in all cultures, and, due to the culture of particular plants, such as peas or beans, it is possible to guarantee organic products and products free of GM technology (non-GMO certificates).

From all industrially used animal proteins, such as milk and whey products, gelatin, chicken egg protein, collagen etc. primarily milk proteins, mainly casein and its salts (e.g., as glue for bottle labels), chicken egg protein as whole protein or albumen as well as egg yolk and proteins isolated from butchery residuals such as gelatin, bone glue and collagen (e.g., in cosmetics products or as adhesive) are used in technology sectors—i.e., in food technology, technical sectors or the like.

Today, plant proteins used on a daily base only come from a limited number of plants. Common isolated legume proteins stem from legumes such as soy, peas, lupines or lentils. Isolates applied on a bigger scale are only soy and wheat proteins, the so-called gluten. Gluten is a problematic protein because many people are allergic to gluten (celiac disease) and there is enormous demand for gluten-free plant protein. Unfractionated soy protein (like many other legume proteins) which is widely used as substitution product for animal protein as well as animal feed, is not indisputable because it contains hormone-active substances. Typical for legumes are Genistein and Daidzein; anti-thyroidoflavones which hem the function of the thyroid. Genistein is 5,7,4'trihydroxyisoflavone with a molecular weight of 270.24 Dalton. Additionally, soy contains protease inhibitors, phytic acid, lectines and soy toxin.

Further isolated legume proteins stem from rape, lupines and lentils. The quality of many commercially available isolated legume proteins, particularly pea proteins, is not yet satisfactory. The reasons for that are versatile. With rape or similar plants it is mainly the fat content of the proteins that causes the rancidness of the proteins and of the products manufactured from that. This also applies to fodder proteins because vegetable fat which has become rancid is stored in animal meat and causes its typical rancid taste.

Another problem of the plant proteins currently available is their strong inherent taste (as with soy protein). Thus, many applications are not possible or the quantities used are restricted, which is also often disadvantageous.

Concerning food applications it must be noted that legume proteins are not wholesome, i.e., they do not contain all amino acids, in particular the 8 so-called essential amino acids the human body cannot produce itself and which must thus be supplied externally. The quality of legume proteins is generally lower than those of animal proteins—but still good.

For producing legume proteins from fruit juice, which is generated by squeezing relevant plant sections, especially fruits, or by liquid/liquid extraction of milled plant parts, mainly two different technical methods are used:

1. Heat coagulation of the proteins in the fruit juice while inactivating the enzymes, or
2. Precipitation of the proteins from the fruit juice at acidic pH or a combination of both.

Separation of the Precipitated Protein

According to the invention plant parts refer to the seeds (e.g., beans, peas, lentils, soy, "Juju" nuts, peanuts etc.) of legumes.

Here, fruit juice refers to both sap squeezed from the seeds and legume protein solutions which are educed from the seeds by use of aqueous mediums. This extraction is necessary whenever the liquid content of the relevant plant part is inappropriate or residual protein needs to be mobilized.

The result of such a typical thermal precipitation by use of which proteins are educed from the fruit juice is a slightly soluble product with insufficient functionalities that is indigestive, has a heavy flavor, and contains harmful substances. With higher temperatures the protein is excessively damaged and its precious characteristics which make it so useful for food industries are increasingly destroyed: neutral taste, bright color, solubility, all other functionalities too, the structure becomes horny and digestibility decreases. This particularly applies to the so-called texturized vegetable protein (TVP), a soy protein which is used as substitute for meat—due to high thermal stresses during the manufacturing process it is difficult to digest and has an extreme bean-like taste.

An additional disadvantage of the procedures known so far for isolating legume proteins is that anti-nutritive substances cannot be removed. This is done by selected elutriation processes with much washing water with often only little quantities of dry substance because they are often hardly soluble. Another possibility is to use expensive solvents that solubilize isoflavones (alcohol) and which need to be regained and reprocessed. Both procedures are very time and cost consuming.

These known legume proteins produced thereby additionally possess only little functionalities and due to their high degree of denaturation, i.e., they are hard to digest and are hardly or not suitable as milk protein substitute. The same applies to proteins of other plants such as wheat, rape, soy etc. which also possess harmful concomitant substances.

Additional typical negative substances coming into being as concomitant substances in precipitated legume proteins are for instance: trypsin inhibitors, proteins inhibiting the proteolytic enzyme trypsin and, thus, also digestion. Trypsin inhibitors can only be rendered harmless by special deactivation processes; in this case by heating treatment at around 70° C.

Additionally, the following substances may occur: Phytic acid (complexes with Ca ions), inhibiting Ca ingestion, lectin and other enzymeinhibitors, digestion inhibitors, tannins/tannic acid inhibiting digestion, ingestion of iron and inactivating digestive enzymes; protease inhibitors, polyphenols and special sugars such as legume sugars which can cause diarrhea.

Additionally, for legumes hormone-like substances are typical, mostly isoflavones. Separating or rendering these substances harmless is today only often done partially—e.g., by elutriating the proteins or by cost and time consuming and/or expensive enzymatic treatments.

Many legume proteins generated by thermal precipitation of protein solutions in alkaline milieus (also including the pasteurization process sometimes necessary) possess higher contents of lysinoalanine, an anti-nutritive condensate whose content should be as low as possible.

It is the problem of the invention to provide legume proteins which possess better functionalities and which avoid the disadvantages of the legume proteins.

According to the invention, the protein is selectively fractionated from aqueous solution by protein-friendly, surprisingly simple methods, which lead to a protein fraction that is suitable for use in food and has adequate functionalities. It is important that, as separation technique for the different proteins, fractionation is used. Fractionation by selective adjustments of pH values and temperatures is an efficient and cheap procedure that allows simple and surprisingly selective protein fractionation on large technical scales.

The fraction according to the invention can also be obtained by gradual membrane filtration or gradual precipitation with solvents or by fractionated separation processes with salt, but consumes significantly more time and costs. It is often advantageous to separate mechanically with decanters which are able to separate large amounts of material into solids and overflow (both continuously and fast).

Particularly pea proteins, field bean proteins and lentil proteins are suitable as quality legume proteins (many essential amino acids).

The legume protein fractions according to the invention are particularly suitable for food, food additives, pharmaceutical additives, animal feed, cosmetic additive, as technical protein, and glue because, on one hand, they are available in adequate quantities and, on the other hand, provide sufficient functionalities due to water solubility.

The selective fractionation of legume protein, as it is available in pea water extract, is carried out with the aim to cheaply isolate the desired fraction from the fruit juice. The method according to the invention is as follows: From one process step to another precipitation conditions are increased in order to isolate fractions with exactly these proteins that have the next lower molecular weight. Here we use the legume protein fractions' different behavior they show depending on the different combinations of temperature and pH value.

According to the invention the method comprises:
Grinding the entire or peeled or otherwise apportioned fruit in order to release the fruit juice enclosed in the cells, if necessary by adding (watery) solvent;
Completely or partially separating the now available fruit juice containing the entire protein from solid substances, and
Fractionated precipitation of protein.

Step 1

The first step is used to separate large proteins. After a first acidic precipitation, it mechanically separates a fraction of the legume protein, the "sediment protein". This has high molecular weight and in a pure protein. Protein of lower molecular weight remains in the supernatant. Thus, cost and time consuming separation of undesired harmful substances by adsorption is avoided in this fraction. Pea protein isolated in this way has a protein content of 90% (N*6.25), has high molecular weight and is thus hardly soluble and functional.

These proteins with a molecular weight of greater than approx. 116 kD can be separated by simply (methods that consume more time and effort such as membrane filtration are regarded as subordinate due to the higher expenses):

centrifuging (once) the pure fruit juice which already has a slightly acidic pH value. Here, the lowest amount of protein is separated, but at least in "mono-fractions" purity or adjusting the acid pH value between pH 2 to 7, preferably between 5-7 and acidic precipitation of the large proteins, whereby the precipitated material is then mechanically separated, for instance by centrifugation. It is important that there will be not too much (which additionally reduces the already very low rate of yield) and not too little (which deteriorates the pureness of the protein of the desired fraction as well as other quality parameters) precipitate.

One particular advantage of these process steps is their extraordinary simplicity, i.e., in terms of machines, materials and energy consumption.

If a protein fraction with a molecular weight greater than 116 kD is to be separated, this can be done by adjusting a pH value suitable for the precipitation and temperature and by controlling these parameters.

Step 2

Here, a target protein fraction of medium molecular weight is isolated by adjusting a pH value which is suitable for precipitation together with a thermal precipitation of the supernatant of step 1 (of course it is possible to use methods that are more time and cost consuming such as membrane filtration). For that, a pH value is selected around the isoelectric point of the protein, in combination with a temperature increase above room temperature.

Accordingly, this complies with the precipitation conditions from the acidic milieu under increased temperatures—accessible at a pH value between 2-6 and 50° C. to 85° C.

Steps 1 and 2 can also be carried out together, whereby a total protein with a molecular weight of greater than approx. 14 kD is then the result.

Surprisingly, by use of the variants according to the invention, which do not require any expensive or complicated processes or process steps and which is very fast, it is possible to achieve the desired target with a combination of simple process steps. Beyond that, the required apparatuses are cheap and operating expenses are low.

It is very advantageous that no chemical additives have to be applied in the process such as enzymes, disinfectants, brighteners.

Concerning the product's characteristics and/or features, it is also surprising that, by means of that fractionation, not only proteins with a special molecular weight range are isolated, but also a fraction that possesses all required characteristics: highly nutritive, neutral color, (nearly) no taste for raw materials, low lysine-alanine contents as well as technological functionalities such as water retention and oil-binding capabilities (emulsifier). This is particularly surprising because the protein fraction precipitated at first is, with peas, is nearly water-insoluble due to the high molecular weight.

By contrast, the bean and pea proteins of the second fraction are soluble in the form of a curve with a broad minimum, of 15 to 70% solubility, depending on the pH value.

In the following, the invention is now described in more detail by means of some examples (to which the invention is by no means restricted).

The legume protein fraction manufactured according to the invention avoids disadvantages of the conventional legume proteins mentioned above (color, bitterness, allergenicity, anti-nutritive products, inherent taste, and loss of functionalities) by elutriating or separating these substances. It is also possible to carry out a fractionated precipitation of 2 protein fractions. Some of the enzymes could be anti-nutritive. These enzymes have a molecular weight amounting to 2 kD to 9 kD so that these are not contained in sufficient numbers in the fraction described here. Beyond that, the heat treatment causes the denaturation and inactivation of enzymes.

Harmful substances: Besides normal environmental toxins such as heavy metals and pesticides only hormone-active substances such as isoflavones and anti-thyroid isoflavones as well as special toxins occur. These substances are separated as described above. Allergic potentials of suchlike legume protein fractions according to the invention with a molecular weight of 14-97 and 100-600 kD are not known. Thus, they are also suitable for producing special allergen-free, vegetable food and cosmetic products.

Measurement of Emulsifying Capacity:

25 g of protein are suspended in 100 g water using an Ultra-turrax. Subsequently, oil is added slowly and in portions while continuing dispersing (e.g., sunflower seed oil, rape oil, olive oil etc.) until the emulsion breaks. The oil-binding and emulsifying capacity is indicated with regard to the concentration of the 3 substances with the maximum oil-binding capacity. 1:4:6 means that a mixture of 1 part protein and 4 parts water can bind 6 parts of oil, i.e., after adding more than 150 g oil to the above mentioned suspension, the test emulsion will break.

Determination of Water-Binding Capacity:

5 g of protein are weighted into 95 g water and the suspension is stirred for 1 h. Then it will be centrifuged (20 min., 3.500 g), the supernatant will carefully be decanted (if necessary the remaining liquid has to be removed by pipettes) and the wet protein will be weighted. (Wet weight–dry weight)/dry weight=water-binding capacity Pea Protein Due to the low water content, peas need to soak (peeled or unpeeled peas) at a pH value of 2-10 over a sufficient time period of from 10 min to several hours, whereby the solution is subsequently pressed or centrifuged, solid substances are separated and the liquid supernatant is used for isolating the protein.

1. Step:

Adjusting the pH of 4.0-7.0 within the extract solution, thus precipitating a pea protein fraction with a molecular weight of approx. 100-600 kD at room temperature and separating the same.

2. Step:

Adjusting the pH of the solution between 4.0 to 6.0 and 50-85° C. (near the isoelectric point), the resulting white precipitate (pH 4-6 for precipitation) is mechanically separated at the above mentioned process conditions with a decanter centrifuge. The protein content of the raw product is approx. 75% in dry substance. These parameters also guarantee the micro-biological pureness of the product, thus an additional pasteurization is not necessary. No high or very high temperatures and acidic milieu, thus little lysine alanine.

Cleaning Steps:

Then, the protein is cleaned to reach isolate quality, i.e., greater than 85% protein in the dry substance. Process parameters: mains water, both cold (room temperature) or hot (preferably 50° C. to 80° C.), pH neutral or acidic to pH 4 to 6. Amount of washing water the same amount or up to twice the amount as the product inflow to the decanter centrifuge. Typically, this process is carried out in two steps, for instance with two decanters which are connected in series, whereby one half of the washing water is supplied in front of the decanter or in the reverse flow, i.e., the entire washing water is supplied in front of the second decanter and discharged from the process in the upper flow section of the first decanter.

It must be observed that, with higher temperatures, the protein will excessively be damaged and its precious characteristics which make it so useful for food industries are increasingly destroyed: neutral taste, light color, solubility, all other functionalities too, the structure becomes horny and digestibility decreases. The protein fraction (remaining in the legume fruit juice) remains soluble even under these increased conditions. Conditions that are not so extreme unnecessarily reduce the yield.

According to SDS-PAGE the molecular weights of the various pea proteins in the high fraction amount to 100-600 kD and in the medium fraction approx. 14-97 kD, whereby the maximum of the proteins is at 20 and blurred from 36.5 to 97 kD, the other bands are generally negligible.

The product of the medium fraction had the following characteristics:
Max. 1% starch
Max. 1% sugar
Max. 1% crude fiber
Isoelectric point: approximately 4.3
pH value of 4.0 to 6.0
Emulsifying capacity: 1:4:10 to 23 (measurement of emulsifying capacity see above)
Solubility—15 to 70% (in water at room temperature and also in hot water dependent on pH value)
Water-binding capacity: 1:4 to 1:5 (test procedures: see above)
Amino acid composition of the obtained pea protein fraction with a molecular weight between 20 and 97 kD was as follows with essential amino acids being underlined:
Ala 3.7-4.2
Arg 7.1 to 7.3
Asp 10.1 to 10.2
Cys 0.9 to 1.0
Glu 14.2 to 14.7
Gly 3.5 to 3.9
His 2.0 to 2.2
Ile 4.1 to 4.6
Leu 7.7 to 8.1
Met 0.9 to 1.2
Phe 5.0 to 5.5
Pro 3.9 to 4.1
Ser 4.2 to 4.6
Thr 3.3 to 3.6
Try 0.8 to 1.0
Tyr 4.0 to 4.20
Val 4.5 to 5.4
Lys 6.3 to 7.6

The entire content of essential amino acids amounts to 32.6% to 36.8%. The sum of the amino acids in the dry substance is 87.1%, in OS 82.2%, raw protein (N*6.25) 85.6% in the dry substance. The fluctuations are typical for natural products. Due to the technical advantages mentioned, this pea protein fraction offers a protein particularly suitable for producing ready-made food.

Field Beans:

With field beans isolation is carried out similar to peas. Contrary to the peas the pH values 4.2-5.3 were equivalent for the precipitation of the fraction with the medium molecular weight. This approaches the isoelectric points of the two main protein fractions (pH 5.5) and (pH 4.8). The medium fraction has a molecular weight between 20 kD and 116 kD, maxima at approx. 36 and, before all, approx. 51 (additional bands at 66, 116 kD, very thin 21 and 23 kD). Amino acid composition of the obtained bean protein fraction with a molecular weight between 20 and 116 kD was as follows with essential amino acids being underlined:
Ala 3.0
Arg 9.5
Asp 119.0
Cys 1.0
Glu 16.1
Gly 3.3
His 2.9
Ile 4.7
Leu 7.9
Met 0.4
Phe 5.1
Pro 6.4
Ser 4.3
Thr 3.2
Try 0.8
Tyr 4.7
Val 4.6
Lys 5.7

The entire content of essential amino acids amounts to 32.4%.

Production of Pea Protein 50 kg peeled peas (of the type *Pisum sativum* L.) have been crushed in a mill and soaked for 0.5 hours at pH 6.0-8.0. Then, the solution containing pea protein was obtained by pressing the soaked ground parts in a decanter. The solution containing the pea protein has been adjusted to a pH value of 5.5 and the precipitated protein has been separated as sediment protein in a sludge separator. The liquid supernatant has then been heated to 80° C. and adjusted to pH 5.0 by precipitating the protein fraction of medium molecular weight. The precipitated protein fraction precipitated that way has been separated in a decanter. The fractions have been washed and the result was 2.5 kg sediment protein and 5 kg medium protein with, in each case, approx. 7% residual moisture content in the form of light powder.

Production of Field Bean Protein

Protein from field beans is produced just like protein from peas. Field bean proteins produced in this way had a medium molecular weight in the range of 20 kD to 116, maxima at approx. 51 and approx. 36. They possess functionalities similar to milk proteins such as casein and can also be used in a similar way.

Use of the pea protein fraction as emulsifying agent in a hypo-allergenic salad dressing 43.2% rapeseed oil have been stirred with 10% salt egg yolk, 34.08% water, 6.00% pea protein, 1.15% NaCl, 7.2% sugar, 0.5% potato fiber, 0.03% paprika, 0.01% carotene, 0.05% white pepper, 7.14% 10% spirit vinegar and 0.64% hot mustard. The result was a hypo-allergenic salad dressing in which it was possible to avoid starch and proteins both of which are usually used as thickening and emulsifying agents. The dressing's emulsifying stability and storability was good and its taste did not cause any complaints.

Use of the pea protein fraction as emulsifying agent in a hypo-allergenic tomato ketchup 30% double concentrated tomato puree, 35.4% water, 9.5% 10% spirit vinegar, 19.00% sugar, 2.3% salt, 2.5% pea protein, 0.5% potato fiber and 0.8% citric acid have been mixed. Here, the result was ketchup free of preservatives which has been obtained by replacing the commonly used wheat starch (for gluten-allergic persons).

Carbohydrate-Reduced Noodle Dough 150 g whole egg, 400 g pea protein, 5 g guar flour, 100 g water, 60 g potato fibers and 6 g salt have been kneaded; the result was noodle dough. This noodle dough has then been formed into noodles and dried. The result was a product with low carbohydrate content, particularly with a small percentage of quickly absorbable carbohydrates; suitable for weight reduction of diabetics.

Protein-Enriched Cream-of-Carrots Soup 300 g carrots, 200 g potatoes, 40 g spring onions, 15 g parsley, 500 g water, 100 g pea protein, 10 g lime juice, 250 g milk, 100 g sour cream, 2 g black pepper and 17 g salt have been mixed resulting in a soup of 1534 g. This soup is ideal for protein-enriched build-up diets.

Coffee Creamer (Cream Substitute)

82.7% water, 10% coconut oil, 5% sugar, 2.25% water-soluble pea protein and 0.05% Xanthan have been properly stirred. The result was a cream-like liquid of neutral taste which can be used as cream substitute particularly as coffee creamer for milk protein and persons who are allergic to lactose.

Beef Patty

85% low-fat beef, 10.65% water, 3% pea protein, 1.2% salt, 0.15% black pepper have been kneaded and meat balls have been formed. Here, the pea protein was used for water retention, to improve the texture and as extender.

Although the invention has been described by means of selective examples, experts will certainly recognize the manifold variations of the invention are possible within the scope of the claims and are also intended to be within the scope of the invention.

What is claimed is:

1. A method of obtaining coagulated legume fruit protein fractions with a molecular weight of greater than 14 kD, comprising the steps of:
    providing fruit juice from legume fruits;
    precipitating a high-molecular-weight legume fruit protein fraction, whose majority has a molecular weight from above 116 kD to about 600 kD by leaving or adjusting the pH the legume fruit juice in the range of 3-6, at a temperature from room temperature up to 40° C.,
    mechanically separating the precipitated high-molecular-weight legume fruit protein fraction from the fruit juice;
    coagulating a medium-molecular-weight legume fruit protein fraction with a molecular weight between about 14 kD-120 kD, with the majority of the molecular weight distribution being between 20 kD and 66 kD, by treating the fruit juice at a pH of 3 to 6 and a temperature between 60 to 90° C.,
    mechanically separating the coagulated medium-molecular-weight legume fruit protein fraction from the fruit juice; and
    washing the coagulated medium-molecular-weight legume fruit protein fraction(s) with water.

2. The method according to claim 1, wherein the medium-molecular-weight legume fruit protein fraction(s) are dried.

3. The method according to claim 1, wherein said washing is carried out with water at a temperature up to 80° C.

4. The method according to claim 3, wherein the washing is carried out at a pH value in the range of the isoelectric point of the protein.

5. The method according to claim 1, wherein the mechanical separation is carried out with a decanter.

6. The method according to claim 1, wherein the separation steps are carried out under oxidation-retardant conditions, selected from the group consisting of adding reducing agents and working under a protective gas.

7. The method according to claim 1, wherein the legume fruit protein is one of a pea protein, field bean protein, lupine protein, and lentil protein.

* * * * *